(12) United States Patent
Sanson et al.

(10) Patent No.: US 8,053,392 B2
(45) Date of Patent: Nov. 8, 2011

(54) AUXIN ACID-CATALYZED STABLE MICROEMULSION PESTICIDE FORMULATION

(75) Inventors: Dale Sanson, Kearney, MO (US); James A. Armbruster, Kansas City, MO (US)

(73) Assignee: PBI/Gordon Corporation, Kansas City, MO (US)

( * ) Notice: Subject to any disclaimer, the term of this patent is extended or adjusted under 35 U.S.C. 154(b) by 1302 days.

(21) Appl. No.: 11/626,212

(22) Filed: Jan. 23, 2007

(65) Prior Publication Data

US 2008/0176921 A1     Jul. 24, 2008

(51) Int. Cl.
*A01N 25/00* (2006.01)
*A01N 63/00* (2006.01)

(52) U.S. Cl. .................................. 504/118; 424/405

(58) Field of Classification Search ................. 424/405; 504/118
See application file for complete search history.

(56) References Cited

U.S. PATENT DOCUMENTS

| | | | |
|---|---|---|---|
| 4,995,900 | A | 2/1991 | Futcher |
| 5,531,995 | A | 7/1996 | Lubetzky et al. |
| 6,232,272 | B1 | 5/2001 | Roberts et al. |
| RE37,313 | E | 8/2001 | Roberts |
| 6,541,424 | B2 | 4/2003 | Roberts et al. |
| 6,689,719 | B2 * | 2/2004 | Jimoh .................... 504/128 |
| 6,803,345 | B2 * | 10/2004 | Herold et al. ............ 504/254 |
| 6,849,579 | B2 * | 2/2005 | Armbruster et al. ....... 504/130 |
| 7,094,735 | B2 | 8/2006 | Herold et al. |

FOREIGN PATENT DOCUMENTS

| | | |
|---|---|---|
| GB | 2267825 | * 12/1993 |
| GB | 2267825 A1 | 12/1993 |

OTHER PUBLICATIONS

Notification of Transmittal of the International Search Report and the Written Opinion of the International Searching Authority or the Declaration of corresponding PCT Application No. PCT/US2008/050784; Document Dated: Jun. 12, 2008; Applicant: PBI/Gordon Corporation et al.; PCT Application Filing Date: Jan. 10, 2008.

* cited by examiner

*Primary Examiner* — Alton Pryor
(74) *Attorney, Agent, or Firm* — Hovey Williams LLP

(57) ABSTRACT

An auxin acid-catalyzed stable microemulsion pesticide formulation is provided that is clear and stable under a wide range of temperature conditions encountered during distribution, storage, and use of the pesticide formulation. A precursor for the microemulsion includes an auxin ester, a protox inhibitor, and an auxin acid stabilizing agent as active ingredients. Inactive ingredients in the precursor include a microemulsifier, a stabilizing co-emulsifier, a dispersant, and a solvent present in amounts such that when the precursor is added to water of dilution to form a concentrate or a ready-to-use formulation, the clear and stable microemulsion that is spontaneously formed has oily active ingredient-containing nano-sized particles no larger than about 1μ dispersed in the water.

40 Claims, 1 Drawing Sheet

AUXIN ACID-CATALYZED STABLE MICROEMULSION PESTICIDE FORMULATION

BACKGROUND OF THE INVENTION

1. Field of the Invention

A precursor is provided for spontaneously forming clear, stable, water-based, acid-catalyzed microemulsion pesticide formulations. The precursor preferably includes as pesticide ingredients an auxin ester, a protox inhibitor, and an auxin acid stabilizing agent. Inactive ingredients in the precursor include a microemulsifier, a stabilizing co-emulsifier, a dispersant, and a solvent present in amounts such that when the precursor is added to water of dilution, a microemulsion is spontaneously formed having particles no larger than about $10\mu$ and that remains clear and is stable under a wide range of temperature conditions typically encountered during distribution, storage, and use of the formulation.

2. Description of the Prior Art

Pesticidal concentrates have long been provided for dilution by a pesticide applicator. Herbicides, for example, available in an oil-based concentrate have included products such as 2,4-D, MCPP, and dicamba, and combinations thereof, along with an emulsifying agent. When the concentrate is added to water of dilution for use, the herbicidal formulation often has a milky appearance and typically must be used in a timely manner to prevent separation of the constituents, particularly where the temperatures encountered during application vary significantly, and especially when the temperature falls outside a level specified by the supplier.

Similarly, organic solvent-based formulations comprised of esters of 2,4-D, MCPA, protox inhibitors, or auxin acids, individually or in various combinations, have been combined with one or more emulsifiers to form macroemulsions where the particles range in size from about $100\mu$ and above when the formulations are added to water of dilution. However, these macroemulsions are not clear and have short-term physical and chemical stability in an aqueous system. Furthermore, the macroemulsion is not formed spontaneously and the macro oil droplets require initial and frequent agitation to remain in suspension in the water.

Pesticidal microemulsions have been developed in the past comprised of one biologically-active oil soluble ingredient, such as bifenthrin, permethrin, or cypermethrin, in combination with one or more microemulsifiers and in certain instances other inert ingredients. However, because only one of these active ingredients is provided in the formulation, physical and chemical stability of the diluted product is generally not a concern because the active ingredient is not prone to hydrolysis. In the instance where an oil soluble hydrolysis-prone pesticide, such as pyraflufen-ethyl (or other ester-based pesticides), is combined with a microemulsifier, the pH of the diluted formulation must be properly adjusted to an acidic level to prevent hydrolysis of the active agent.

Pesticidal microemulsions have also been provided in the past comprised of an active oil soluble ingredient, such as carfentrazone-ethyl, in conjunction with a water soluble active salt such as glyphosate, and one or more microemulsifiers. In this instance, when the formulation is diluted with water, the glyphosate is soluble in the solute, and the carfentrazone-ethyl is not prone to hydrolysis because the glyphosate is sufficiently acidic to lower the pH of the microemulsion to a level preventing such hydrolysis. An exemplary formulation is described in U.S. Pat. No. 6,689,719. In this example, although the carfentrazone-ethyl is microemulsified, the glyphosate salt remains in the continuous water phase.

Heretofore, it has not been practical to provide a pesticide precursor that includes a number of oil soluble active ingredients that spontaneously form a chemically and physically stable microemulsion in which the particles are $10\mu$ or less. The formulation of microemulsions is an inexact science and, for the most part, eludes prediction. Many oils do not microemulsify, regardless of how much excess emulsifier is employed. The most significant difference between a macroemulsion and a microemulsion is that increasing the amount of emulsifier in a macroemulsion usually improves stability, but this is not true for microemulsions. Formation of a microemulsion is largely dependent upon specific and incompletely understood interactions between the molecules of oil, emulsifiers, and water. If required interactions do not occur, no amount of excess emulsifiers will produce a microemulsion. On the other hand, when the oil, emulsifier, and water interact in a specific interdependent manner, and the correct proportions of each are present, microemulsions can form spontaneously.

SUMMARY OF THE INVENTION

This invention relates to a precursor for an acid-catalyzed, physically and chemically stable microemulsion pesticide formulation that includes at least three different pesticide active ingredients, which collectively function in an effective, efficacious manner when diluted with water for use. Preferably, the precursor includes an auxin ester, a protox inhibitor, and one or two auxin acid stabilizing agents, all of which are active pesticides. Inactive ingredients are provided that cause the active agents in the precursor to spontaneously form a microemulsion wherein the particles are no larger than about $10\mu$, and preferably no more than about $1\mu$, when the precursor is added to dilution water. The precursor is clear, and remains clear and stable over an extended period of time under widely varying temperature conditions during distribution and storage, and retains its clarity and stability when diluted for use.

The inactive ingredients in the precursor preferably include a microemulsifier, an interfacial polymeric stabilizing co-emulsifier, a dispersant, and a solvent. When the precursor is added to water, a microemulsion is spontaneously formed in which the auxin ester, the protox inhibitor, and the auxin acid stabilizing agent are dissolved in the solvent and the microemulsifier and co-emulsifiers contribute to formation of oilynano-sized liquid droplets. The stability of the dispersion of these nano-sized oily droplets is enhanced by the auxin acid stabilizing agent. It has unexpectedly been discovered that the acid auxin stabilizer, even though it is an active ingredient incorporated in respective nano-sized particles, ionizes and imparts negative charges to the individual nano-sized droplets and positive charges to the water molecules. The negative charges contribute to the nano-sized particles being repelled from one another, thereby enhancing the physical stability of the of the microemulsion droplets by preventing coalescence.

In addition, the stability and integrity of the individual nano-sized auxin oil droplets containing dissolved auxin ester pesticide is further enhanced by the incorporation of a microemulsifier and an interfacial stabilizing co-emulsifier. The microemulsifier has molecular moieties that exhibit both lipophilic and hydrophilic characteristics. The lipophilic portions of the microemulsifier molecules are embedded in the individual nano-sized oil droplets, while the hydrophilic portions of the microemulsifier molecules project outwardly from respective droplets into the surrounding continuous water phase. The polymeric stabilizing co-emulsifier molecules adhere to the surface of the nano-sized oil droplets between the microemulsifier molecules, thereby tending to maintain the spacing between adjacent microemulsifier molecules to prevent coalescence of the droplets and therefore enhance the physical stability of the microemulsion.

In a preferred embodiment of the invention, a water soluble polymeric dispersant is also incorporated in the precursor. The dispersant molecules, when dissolved in water, because of their size and numerous side chains, further add to the microemulsion stability by providing stearic hindrance against agglomeration and coalescence of the nano-sized particles containing the auxin ester, protox inhibitor, and auxin acid stabilizing agent.

DETAILED DESCRIPTION OF THE PREFERRED EMBODIMENT

Figure 1:
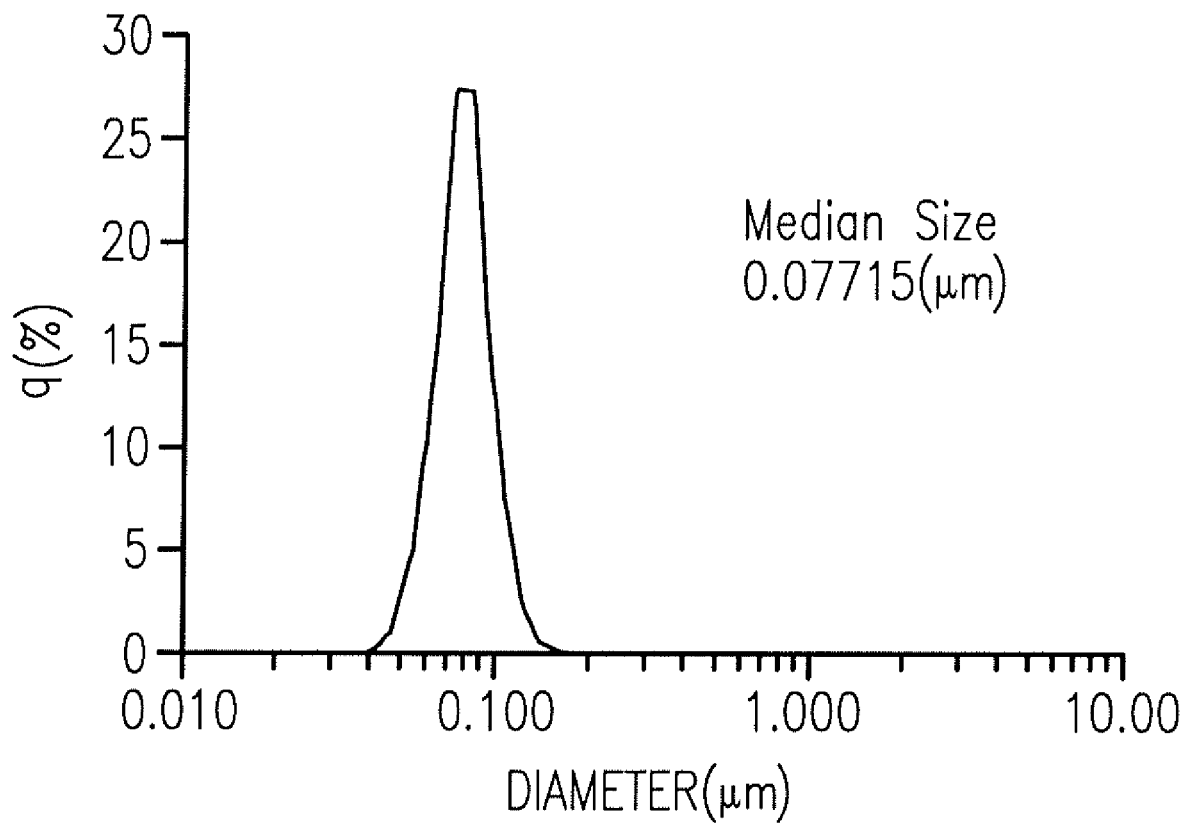
FIG. 1 is a representative mean value graph of the particle size distribution of a sample of a preferred microemulsion pesticide concentrate formulation of this invention. The sample was tested using a Horiba LA950 laser scattering particle size distribution analyzer.

The preferred microemulsion pesticide formulation of this invention is prepared from a precursor containing a biologically effective quantity of active pesticide ingredients, including an auxin ester, a protox inhibitor compatible with the auxin ester, and an auxin acid stabilizing agent. Microemulsion-forming inactive ingredients are incorporated in the precursor, that include a microemulsifier, a stabilizing co-emulsifier for the pesticides, and a solvent for assisting in dissolving the pesticide active ingredients of the concentrate formulation. In addition, a dispersant for the pesticides may also be incorporated in the microemulsion-forming ingredients. The amount of the inactive ingredients is sufficient with respect to the quantity of the active pesticide ingredients to cause the precursor to spontaneously form a microemulsion wherein the particles are no larger than about 10μ, and preferably smaller than 1μ, when the precursor is diluted with water to form a microemulsion concentrate. A sufficient amount of the auxin acid stabilizing agent is present to form overall net negative repulsion charges on the particles to prevent coalescence of the microemulsion particles to maintain the physical stability of the microemulsion and to adjust the pH of the continuous water phase to a level to maintain the chemical stability of the microemulsion.

The precursor, which is clear when added to a quantity of water, forms a clear, time and temperature stable microemulsion concentrate formulation, that is then distributed to consumers for further dilution before use. Typically, the concentration of the precursor in the water-based concentrate is from about 10% to about 20% by weight. Clear and time and temperature stable microemulsion ready-to-use formulations (RTUs) distributed to users will nominally contain from about 0.2% to about 1% by weight of the precursor in water.

The amount of the precursor in a concentrate formulation containing water of dilution may be of the order of 0.5% to about 50% by weight. Typically, the formulation will contain an amount of precursor in the range of about 1% to about 20% by weight, with the most preferred amount of precursor being about 15%.

The ratio of the active pesticide ingredients to the inactive emulsifier and co-emulsifier agents is within the range of from about 1 to about 3.5, and preferably within the range of from about 1.3 to about 3, and most preferably within the range of from about 1.7 to about 2.5.

The auxin ester is a linear or branched hydrocarbon ester having $C_1$-$C_{12}$ carbon atoms. Exemplary auxin esters are selected from the group consisting of 2,4-D 2-ethyl hexyl ester, and esters of 2,4-D, 2,4-DP, MCPP, MCPB, MCPA, triclopyr, picloram, 2,4-DB, fluoroxypyr, aminopyralid, clopyralid, and the optical isomers of MCPP, MCPB, and 2,4-DP. Preferred auxin esters are esters of 2,4-D, MCPP, and triclopyr. The precursor preferably includes from about 20% to about 40% by weight of the auxin ester, and is most preferably about 35% by weight.

The protox inhibitor is an active ingredient compatible with the auxin ester and is selected from the group consisting of pyraflufen-ethyl, flumiclorac-pentyl, flumioxazin, fluthiacet-methyl, aclonifen, bifenox, chlornitrophen, ethoxyfen, fluoroglycofen-ethyl, fomesafen, lactofen, oxyfluorfen, azafendin, cinidon-ethyl, oxadiargyl, oxadiazon, pentoxazone, flumipropyn, flupropacil, benzfendizone, nipyraclofen, fluazolate, thidiazimin, a triazalone, and a compound having the structural formula $$\text{[structural formula]}$$

or combinations thereof. Especially preferred protox inhibitors are pyraflufen-ethyl or a triazalone. The precursor preferably includes from about 0.5% to about 3% by weight of the protox inhibitor, and is most preferably about 2% by weight.

The auxin acid stabilizing agent is selected from the group consisting of 2,4-D, 2,4-DP, dicamba, MCPP, MCPB, MCPA, triclopyr, picloram, quinclorac, 2,4-DB, fluoroxypyr, aminopyralid, clopyralid, and the optical isomers of MCPP, MCPB, and 2,4-DP. The preferred auxin acid stabilizing agent is dicamba and/or an optical isomer of MCPP (also referred to as R+MCPP or $MCPP_P$). The precursor preferably includes from about 5% to about 12% by weight of the auxin acid stabilizing agent, more preferably from about 7% to about 12%, and most preferably from about 10% to about 12% by weight of the auxin acid stabilizing agent, with the preferred auxin acid stabilizing agent being a combination of dicamba and an optical isomer of MCPP.

The inactive microemulsion-forming ingredients preferably include from about 25% to about 35% by weight of a microemulsifier, from about 8% to about 12% by weight of a stabilizing co-emulsifier for the pesticides, and from about 7% to about 12% by weight of a solvent for the pesticides. A blend of specific anionic and non-ionic emulsifiers has been found to provide both elevated as well as lower temperature physical stability.

The microemulsifier is preferably selected from the group consisting of alkyl ethoxylates, alkylated alkyl phenols, substituted ionic or nonionic mono-, di-, and tristearyl phenol ethoxylates, and dodecylbenzene sulfonates. A particularly preferred emulsifier is a saturated or unsaturated, straight chain or branched, or hydroxylated straight chain or branched castor oil ethoxylate having 5-45 moles of ethoxylation, and most preferably castor oil ethoxylate having 30 moles of ethoxylation, that may be obtained from Harcros Chemical, Kansas City, Kans., as Crystal Inhibitor #5.

The inactive agents include a stabilizing co-emulsifier selected from the group consisting of anionic, and non-ionic random, graft, comb, and block copolymers. A preferred random copolymer is Atlox 4914 of Uniqema that has an HLB value of from about 5 to about 7. An exemplary graft copolymer co-emulsifier is methyl methacrylate copolymer. Useful graft and comb copolymers having essentially the same emulsifying properties are interchangeable in the present invention. The block copolymer co-emulsifier preferably has an HLB value of from about 5 to about 10, with a preferred block co-emulsifier being a hydrophilic lipophilic AB block copolymer, such as polyethylene glycol ether (Atlox G5000), having an HLB value of about 16.9, thereby providing broader microemulsion temperature stability. The co-emulsifier constituent stabilizes the interfacial surfaces of the oil droplets.

Although Atlox G5000 is preferred as the co-emulsifier, alternatively, a calcium alkylbenzene sulfonate, such as Toximul 3409F may be incorporated in the formulation for enhanced temperature stability of the system. Other anionic surfactants selected from the group consisting of amine, magnesium, potassium, sodium, and zinc salts of alkylbenzene sulfonates, alkylated polyarylphenol phosphate salts, and alkyl naphthalene sulfonates each having an HLB greater than 10, may be used as stabilizing co-emulsifiers.

A dispersant may be included in the inactive additives of the precursor for its dispersant properties. A comb copolymer having an HLB value of from about 5 to about 10 is a suitable dispersant, with Atlox 4913 of Uniqema, having an HLB value of from about 11 to about 12, being preferred. Inclusion of Atlox 4913 at a concentration of from about 3% to about 5% by weight in the precursor is believed to assist in steric interference with coalescence of the nano-sized oily particles.

Suitable solvents are preferably selected from the group consisting of ethers, glycols, and aromatic solvents. One useful solvent is Dowanol (propylene glycol monomethyl ether). Other exemplary solvents may be selected from the group consisting of alkyl glycol ethers, aprotic heterocyclic or mono, di-, or polycyclic aromatic solvents having $C_2$-$C_{25}$ carbon atoms, cyclohexanol, hexanol, octanol, butyl glycol, $C_2$-$C_{25}$ mono- and diglycols, polyethylene glycol, glycerol, and $C_3$-$C_{10}$ alkyl carbonates including a propylene carbonate such as JeffSol AG-1555.

When the precursor is incorporated in a quantity of water to form a concentrate or an RTU, the auxin ester, which is an oil at room temperature, spontaneously disperses as a microemulsion of oily droplets in the continuous water phase that are of unexpectedly small median sizes. The oily droplets have a median diameter of less than about 0.1 μm, and nominally a median diameter from about 0.05 to about 0.07 μm. The greater the overall surface area of the droplets of the microemulsion, the greater the stability of the formulation.

The protox inhibitor is dissolved in the nano-sized auxin ester microemulsion oily droplets. The auxin acid stabilizing agent, which is a solid at room temperature, is also incorporated into the oily auxin ester droplets. Lipophilic heads of the microemulsifier are attracted to and are incorporated into individual oil droplets, while the hydrophilic tails of the microemulsifier project outwardly from the oil droplets into the continuous water phase. The co-emulsifier is believed to irreversibly adhere to the oil droplet surfaces between the tails of the microemulsifier to thereby maintain separation of the microemulsifier tails, thereby enhancing physical stability of the microemulsion.

When the precursor is added to water to form a microemulsion concentrate, the pH of the solution has been found to be about three because of the presence of the auxin acid stabilizing agent. Protox inhibitor pesticides tend to hydrolyze when added to water. Therefore, it is preferred that when preparing a concentrate formulation from the precursor, a basifying agent be added to the water of dilution in order to adjust the pH of the microemulsion to a level of from about 5 to about 6. Maintenance of the pH of the concentrate at a pH of from 5 to 6 optimizes chemical stability of the protox inhibitor. If the pH of the concentrate were allowed to fall below about 5, the physical stability of the microemulsion would be compromised because of migration of the auxin acid stabilizing agent from the oil droplets into the continuous water phase, resulting in irreversible precipitation of the auxin acid stabilizing agent in the water.

A suitable quantity of a basifying agent should be added to the concentrate water to bring the pH of the formulation to the requisite 5 to 6 level. Exemplary basifying agents include those selected from the group of mineral bases (KOH, NaOH, etc.), organic nitrogen bases of linear and branched $C_1$-$C_9$ alkyl amines such as dimethyl amine, triethylamine, and isopropylamine, and organic heterocyclic amine bases of $C_4$-$C_{10}$ compounds containing $N_1$-$N_3$ such as 1,2-benzisothiazolin-3-one.

The auxin acid stabilizing agent, which is also incorporated in the individual oily nano-sized droplets, undergoes ionization with proton charges being attracted to the surrounding phase. As a result, there is an overall net negative charge on each individual oily droplet. This causes net repulsive forces among adjacent oily droplet preventing droplet coalescence. The pH of the basified concentrate, which is initially about 6, tends to drift lower by one-half pH unit during storage for a period of at least two months. This decrease in pH, as demonstrated by the tests recorded in Table 1, establishes that there is a migration of protons from the auxin acid stabilizing agent in the oily droplets to the continuous water phase, further contributing to physical stability of the concentrate.

TABLE 1

| Actives | AI % | pH/ date measured |
|---|---|---|
| 2,4-D Acid | 6.60% | pH 5.60/Nov. 29, 2005 |
| Dicamba | 0.337% | |
| Pyraflufen-ethyl | 0.343% | pH 5.41/Sep. 12, 2006 |
| 2,4-D Acid | 7.20% | pH 5.65/Nov. 29, 2005 |
| Dicamba | 3.71% | |
| Pyraflufen-ethyl | 0.37% | pH 5.20/Sep. 11, 2006 |
| 2,4-D Acid | 5.40% | pH 5.56/Nov. 29, 2005 |
| R(+)MCPP | 0.974% | |
| Pyraflufen-ethyl | 0.279% | pH 5.12/Sep. 12, 2006 |
| 2,4-D Acid | 6.00% | pH 5.55/Nov. 29, 2005 |
| R(+)MCPP | 1.08% | |
| Pyraflufen-ethyl | 0.31% | pH 5.08/Sep. 12, 2006 |
| 2,4-D Acid | 6.60% | pH 5.56/Nov. 29, 2005 |
| R(+)MCPP | 1.19% | |
| Pyraflufen-ethyl | 0.34% | pH 5.09/Sep. 12, 2006 |
| 2,4-D Acid | 7.18% | pH 5.58/Nov. 29, 2005 |
| R(+)MCPP | 1.30% | |
| Pyraflufen-ethyl | 0.37% | pH 4.71/Sep. 11, 2006 |
| 2,4-D Acid | 0.86% | *pH ~7/Nov. 29, 2005 |
| R(+)MCPP | 0.31% | |
| Dicamba | 0.09% | pH 6.72/Sep. 12, 2006 |
| Pyraflufen-ethyl | 0.012% | |
| 2,4-D Acid | 1.73% | *pH ~7/Nov. 29, 2005 |
| R(+)MCPP | 0.62% | |

TABLE 1-continued

| Actives | AI % | pH/ date measured |
|---|---|---|
| Dicamba | 0.18% | pH 6.19/Sep. 12, 2006 |
| Pyraflufen-ethyl | 0.024% | |
| 2,4-D Acid | 2.57% | *pH ~7/Nov. 29, 2005 |
| R(+)MCPP | 0.93% | |
| Dicamba | 0.27% | pH 5.86/Sep. 12, 2006 |
| Pyraflufen-ethyl | 0.036% | |

Physical stabilization of the spontaneously-formed microemulsion when the precursor is added to water by incorporation of an auxin acid stabilizing agent in the formulation was confirmed by tests comparing a two-active ingredient microemulsion formula (protox inhibitor plus 2,4-D 2EHE) against two four-way microemulsion formulations (2,4-D acid, R+MCPP, dicamba, and pyraflufen-ethyl). After six months of ambient storage, the cloudiness of the two-way formulation was found to be greater than the four-way formulations, demonstrating that the auxin acid stabilizing agent increased the physical stability of the microemulsion formulation. Cloudiness was quantitatively measured using a UV/VIS Spectrophotometer.

TABLE 2

| Active Ingredients (AI) | AI % | Elapsed Time | % Transmittance Change from Initial Measurement* |
|---|---|---|---|
| 2,4-D | 3.60 | 6 Months | +6.60 |
| Pyraflufen-ethyl | 0.19 | | |
| 2,4-D | 3.60 | 6 Months | +1.40 |
| R(+)MCPP | 0.65 | | |
| Pyraflufen-ethyl | 0.19 | | |
| 2,4-D | 3.60 | 6 Months | +2.25 |
| R(+)MCPP | 0.65 | | |
| Dicamba | 0.20 | | |
| Pyraflufen-ethyl | 0.19 | | |

*The % Transmittance values found in Table 2 are compared to the initial values. An increase in percent transmittance indicates increased cloudiness.

In a preferred precursor formulation, the active ingredients comprise on a weight basis from about 1% to about 10% of active ingredients, from about 5% to about 30% of an emulsifier, from about 2% to about 20% of a co-surfactant, from about 5% to about 10% of a solvent, and from 0.05% to about 0.5% of a biostat.

A precursor and microemulsion concentrate containing three active ingredients may be prepared by combining, on a weight basis:

EXAMPLE 1

| Ingredients | Precursor | Microemulsion Concentrate |
|---|---|---|
| 2,4-D 2EHE | 35.51% | 11.45% |
| Dicamba | 1.27% | 0.41% |
| Pyraflufen-ethyl | 1.27% | 0.41% |
| castor oil ethoxylate | 42.36% | 13.66% |
| Atlox G5000 | 5.68% | 1.83% |
| Atlox 4913 | 4.26% | 1.37% |
| Dowanol | 9.74% | 3.14% |
| Water | | 67.73% |
| Total Active Ingredients: | | 7.94% |
| Total Emulsifier Load: | | 16.87% |
| Ratio Emulsifier/Actives: | | 2.12 |

EXAMPLE 2

| Ingredients | Precursor | Microemulsion Concentrate |
|---|---|---|
| 2,4-D 2EHE | 35.49% | 5.66% |
| Dicamba | 1.26% | 0.20% |
| Pyraflufen-ethyl | 1.26% | 0.20% |
| castor oil ethoxylate | 42.28% | 6.74% |
| Atlox G5000 | 5.66% | 0.90% |
| Atlox 4913 | 4.26% | 1.37% |
| Dowanol | 9.79% | 1.56% |
| Water | | 84.06% |
| Total Active Ingredients: | | 3.98% |
| Total Emulsifier Load: | | 8.32% |
| Ratio Emulsifier/Actives: | | 2.09 |

A precursor and microemulsion concentrate containing four active ingredients may be prepared by combining, on a weight basis:

EXAMPLE 3

| Ingredients | Precursor |
|---|---|
| 2,4-D 2EHE | 34.15% |
| Dicamba | 2.20% |
| Pyraflufen-ethyl | 1.38% |
| R(+)MCPP | 4.33% |
| castor oil ethoxylate | 34.61% |
| Atlox G5000 | 9.85% |
| Atlox 4913 | 4.07% |
| Dowanol | 9.39% |

EXAMPLE 4

The precursor of Example 3 was diluted with water to form a concentrate containing 18.41% of the precursor formulation, 80.99% of water, 0.1% of Dowacil 75, and 0.50% of 98% diethanolamine. FIG. 1 is a graphical representation of an analysis of the concentrate formulation of this Example using the Horiba LA 950 particle size distribution analyzer. The median size of the particles was found to be of the order of 0.07715 μm. Particle size tests of other formulations with the Horiba LA 950 equipment gave median particle sizes of the order of no more than about 0.05 μm.

EXAMPLE 5

The precursor of Example 3 was diluted with water to form a concentrate containing 14.91% of the precursor formulation, 84.54% of water, 0.11% of Dowacil 75, and 0.44% of 98% diethanolamine. The median size of the particles of this formulation using the Horiba LA 950 equipment was 0.7799 μm.

EXAMPLE 6

The precursor of Example 3 was also diluted with water to form an RTU formulation containing 0.57% of the precursor formulation, 99.31% of water, and 0.12% of proxel GXL.

EXAMPLE 7

| Ingredients | Precursor | Microemulsion Concentrate |
|---|---|---|
| 2,4-D 2EHE | 34.47% | 11.46% |
| Dicamba | 1.20% | 0.40% |
| Pyraflufen-ethyl | 1.20% | 0.40% |
| R(+)MCPP | 4.33% | 1.44% |
| castor oil ethoxylate | 35.13% | 11.68% |
| Atlox G5000 | 10.00% | 3.33% |
| Atlox 4913 | 4.13% | 1.37% |
| Dowanol | 9.53% | 3.17% |
| Water | | 66.75% |
| Total Active Ingredients: | | 9.27% |
| Total Emulsifier Load: | | 16.38% |
| Ratio Emulsifier/Actives: | | 1.77 |

EXAMPLE 8

| Ingredients | Precursor | Microemulsion Concentrate |
|---|---|---|
| 2,4-D 2EHE | 34.47% | 5.73% |
| Dicamba | 1.20% | 0.20% |
| Pyraflufen-ethyl | 1.20% | 0.20% |
| R(+)MCPP | 4.33% | 0.72% |
| castor oil ethoxylate | 35.13% | 5.84% |
| Atlox G5000 | 10.00% | 1.66% |
| Atlox 4913 | 4.13% | 0.69% |
| Dowanol | 9.53% | 1.58% |
| Water | | 83.37% |
| Total Active Ingredients: | | 4.64% |
| Total Emulsifier Load: | | 8.19% |
| Ratio Emulsifier/Actives: | | 1.77 |

A RTU microemulsion formulation and precursor containing four active ingredients may be prepared by combining, on a weight basis:

EXAMPLE 9

| Ingredients | Precursor | Microemulsion Concentrate |
|---|---|---|
| 2,4-D 2EHE | 34.15% | 0.195% |
| Dicamba | 2.20% | 0.013% |
| Pyraflufen-ethyl | 1.38% | 0.008% |
| R(+)MCPP | 4.33% | 0.025% |
| castor oil ethoxylate | 34.61% | 0.197% |
| Atlox G5000 | 9.85% | 0.056% |
| Atlox 4913 | 4.07% | 0.023% |
| Dowanol | 9.39% | 0.054% |
| Water | | 99.43% |
| Total Active Ingredients: | | 0.161% |
| Total Emulsifier Load: | | 0.277% |
| Ratio Emulsifier/Actives: | | 1.72 |

EXAMPLE 10

| Ingredients | Precursor | Microemulsion Concentrate |
|---|---|---|
| 2,4-D 2EHE | 34.15% | 0.290% |
| Dicamba | 2.20% | 0.019% |
| Pyraflufen-ethyl | 1.38% | 0.012% |
| R(+)MCPP | 4.33% | 0.037% |
| castor oil ethoxylate | 34.61% | 0.294% |
| Atlox G5000 | 9.85% | 0.084% |
| Atlox 4913 | 4.07% | 0.035% |
| Dowanol | 9.39% | 0.080% |
| Water | | 99.15% |
| Total Active Ingredients: | | 0.24% |
| Total Emulsifier Load: | | 0.41% |
| Ratio Emulsifier/Actives: | | 1.69 |

Chemical stability tests were conducted on four-way active ingredient microemulsion formulations at 40° C. for one month to determine the active ingredient percent difference at the end of one month.

EXAMPLE 11

| Actives | Active Ingredients (AI) % | Chemical Stability |
|---|---|---|
| 2,4-D 2EHE | 8.49% | +1.25% |
| Triclopyr | 2.17% | +1.94% |
| Dicamba | 0.84% | +1.06% |
| Pyraflufen-ethyl | 0.20% | +1.44% |

EXAMPLE 12

| Actives | Active Ingredients (AI) % | Chemical Stability |
|---|---|---|
| 2,4-D 2EHE | 2.33% | +2.02% |
| Triclopyr | 0.60% | +2.38% |
| Dicamba | 0.23% | +1.71% |
| Pyraflufen-ethyl | 0.06% | −0.90% |

Other formulations were subjected to accelerated chemical stability tests at a temperature of 40° C. for a period of one month to determine total chemical stability of the active ingredients.

EXAMPLE 13

| Actives | Active Ingredients (AI) % | Pyraflufen-ethyl Chemical Stability |
|---|---|---|
| 2,4-D acid | 9.0% | |
| Dicamba | 0.52% | |
| Pyraflufen-ethyl | 0.6% | +5.89% |

EXAMPLE 14

| Actives | Active Ingredients (AI) % | Pyraflufen-ethyl Chemical Stability |
|---|---|---|
| 2,4-D acid | 9.0% | |
| R(+)MCPP | 1.63% | |
| Pyraflufen-ethyl | 0.6% | +1.05% |

EXAMPLE 15

| Actives | Active Ingredients (AI) % | Pyraflufen-ethyl Chemical Stability |
|---|---|---|
| 2,4-D acid | 9.0% | |
| R(+)MCPP | 1.63% | |
| Dicamba | 0.52% | |
| Pyraflufen-ethyl | 0.6% | +1.07% |

EXAMPLE 16

| Actives | Active Ingredients (AI) % | Pyraflufen-ethyl Chemical Stability |
|---|---|---|
| 2,4-D acid | 9.0% | |
| Pyraflufen-ethyl | 0.1% | +0.93% |

Only the chemical stability of pyraflufen-ethyl was analyzed because of its susceptibility to hydrolysis, as set forth in Examples 13-16.

One of the attributes of the microemulsion formulations of the present invention is their low volatile organic content (VOC). The VOC emission potential of the concentrate of Example 4 was found to be about 1.5%; the VOC emission potential of the concentrate of Example 5 was found to be 1.11%; and the VOC emission potential of the concentrate of Example 6 was determined to be no more than about 0.3%. In California, having one of the most stringent VOC emission regulations, a VOC below 20% is acceptable. The formulations of the present invention have a VOC emission potential of less than 2%.

It was found that a microemulsion formulation of this invention containing 2,4-D ester, MCPP-p, dicamba, and pyraflufen-ethyl was equally efficacious as an emulsifiable concentrate containing the same active ingredients. This result was demonstrated by seven day weed control tests of different weeds treated with respective herbicidal formulations.

TABLE 3

| Treatment | Rate (pts/A) | Dandelion | Plantain | Clover |
|---|---|---|---|---|
| 0.7 lbs 2,4-D Ester + 0.24 lbs MCPP-p + 0.07 lbs dicamba + 0.008 lbs Pyraflufen/gal - Microemulsion | 8 | 6.0[1] | 5.0 | 4.7 |
| 0.7 lbs 2,4-D Ester + 0.24 lbs MCPP-p + 0.07 lbs dicamba + 0.008 lbs Pyraflufen/gal - Emulsifiable Concentrate | 8 | 6.0 | 5.3 | 4.3 |
| Untreated Control | — | 1.0 | 1.0 | 1.0 |

[1]Weed Control Ratings 1-9 with 1 = no control and 9 = total control.

The precursor and microemulsion formed therefrom of this invention are unique in a number of significant respects:

1) The microemulsion contains as many as four active ingredients and is physically and temperature stable.

2) The microemulsion contains one or more active ingredients that are oils at room temperature with one or more active ingredients that are solids at room temperature. The solid active ingredients are stabilized in the micro-oil droplets and do not migrate to the water phase. Hence, there is no precipitation out of the active ingredients from the solution under varying temperature conditions and over extended time storage intervals.

3) The physical stability of the multiple active ingredient microemulsion is enhanced by the incorporation of a solid auxin acid stabilizing agent, which is relatively more acidic. This results in hydrogen ion donation from the oil droplets to the water phase, increasing the overall negative potential of the micro-oil droplets. This causes an increased negative charge of the micro-oil droplets and a net repulsion of all of the micro-oil droplets in the water phase as a result of the same charge potential.

4) A four active ingredient microemulsion system is provided in which a protox inhibitor prone to hydrolysis is chemically stabilized with no appreciable hydrolysis occurring as a result of the incorporation of the auxin acid stabilizing agent.

5) The spontaneous pH decrease of the microemulsion from proton donation from the micro-oil droplets enhances the chemical stability of a protox inhibitor in the formulation.

6) A method is provided for dissolving the solid active ingredients in the oil pesticide constituents in which stable oil droplets are spontaneously formed without migration of the solid active ingredients incorporated in the oily droplets from the oil to the water phase.

We claim:

1. A precursor composition for a stable water based microemulsion pesticide formulation comprising the combination of:
   a quantity of active pesticide ingredients including from about 20% to about 40% by weight of an auxin ester, from about 0.5% to about 3% by weight of a protox inhibitor compatible with the auxin ester, and from about 5% to about 12% by weight of an auxin acid stabilizing agent; and
   an amount of inactive agents including from about 25% to about 35% by weight of a microemulsifier, from about 8% to about 12% by weight of a stabilizing co-emulsifier for the pesticides, and from about 7% to about 12% by weight of a solvent for the pesticides, the amount of the inactive ingredients being sufficient relative to the quantity of the active pesticide ingredients to cause the precursor composition to spontaneously foam a microemulsion having particles that are no larger than 10μ when the precursor composition is diluted with water.

2. The precursor composition as set forth in claim 1, wherein is included from about 3% to about 5% by weight of a dispersant for the pesticides.

3. The precursor composition as set forth in claim 1, wherein the ratio of the active pesticide ingredients to the inactive microemulsifier and co-emulsifier agents is within the range of from about 1 to about 3.5.

4. The precursor composition as set forth in claim 1, wherein the ratio of the active pesticide ingredients to the inactive microemulsifier and co-emulsifier agents is within the range of from about 1.3 to about 3.

5. The precursor composition as set forth in claim 1, wherein the ratio of the active pesticide ingredients to the inactive microemulsifier and co-emulsifier agents is within the range of from about 1.7 to about 2.5.

6. The precursor composition as set forth in claim 1, wherein the auxin ester is selected from the group consisting of 2,4-D 2 ethyl hexyl ester and esters of 2,4-D, 2,4-DP, MCPP, MCPB, MCPA, triclopyr, picloram, 2,4-DB, fluoroxypyr, aminopyralid, clopyralid, and the optical isomers of MCPP, MCPB, and 2,4-DP.

7. The precursor composition as set forth in claim 6, wherein the auxin ester is a linear or branched hydrocarbon ester having $C_1$-$C_{12}$ carbon atoms.

8. The precursor composition as set forth in claim 1, wherein said protox inhibitor is selected from the group consisting of pyraflufen-ethyl, flumiclorac-pentyl, flumioxazin, fluthiacet-methyl, aclonifen, bifenox, chlornitrophen, ethoxyfen, fluoroglycofen-ethyl, fomesafen, lactofen, oxyfluorfen, azafendin, cinidon-ethyl, oxadiargyl, oxadiazon, pentoxazone, flumipropyn, flupropacil, benzfendizone, nipyraclofen, fluazolate, thidiazimin, a triazalone, and a compound having the structural formula and combinations thereof.

9. The precursor composition as set forth in claim 1, wherein said protox inhibitor is pyraflufen-ethyl.

10. The precursor composition as set forth in claim 1, wherein said auxin ester is 2,4-D 2-ethyl hexyl ester.

11. The precursor composition as set forth in claim 1, wherein said auxin acid stabilizing agent is selected from the group consisting of 2,4-D, 2,4-DP, dicamba, MCPP, MCPB, MCPA, triclopyr, picloram, quinclorac, 2,4-DB, fluoroxypyr, aminopyralid, clopyralid, and the optical isomers of MCPP, MCPB, and 2,4-DP.

12. The precursor composition as set forth in claim 1, wherein said auxin acid stabilizing agent is dicamba.

13. The precursor composition as set forth in claim 1, wherein said auxin acid stabilizing agent is MCPP.

14. The precursor composition as set forth in claim 1, wherein said microemulsifier is a hydrophilic lipophilic emulsifier having an HLB value greater than 10.

15. The precursor composition as set forth in claim 14, wherein said microemulsifier is selected from the group consisting of alkyl ethoxylates, alkylated alkyl phenols, substituted ionic or nonionic mono-, di-, and tristearyl phenol ethoxylates, and dodecylbenzene sulfonates.

16. The precursor composition as set forth in claim 15, wherein said microemulsifier is an alkyl ethoxylate wherein the alkyl ethoxylate is a saturated or unsaturated, straight chain or branched, or hydroxylated straight chain or branched castor oil ethoxylate having from 5-45 moles of ethoxylation.

17. The precursor composition as set forth in claim 16, wherein said alkyl ethoxylate is castor oil ethoxylate having 30 moles of ethoxylation.

18. The precursor composition as set forth in claim 15, wherein said microemulisfier ethoxylate is a stearyl phenol ethoxylate.

19. The precursor composition as set forth in claim 1, wherein said stabilizing co-emulsifier is selected from the group consisting of anionic, and non-ionic random, graft, comb, and block copolymers.

20. The precursor composition as set forth in claim 19, wherein said stabilizing co-emulsifier is a random copolymer has an HLB value of from about 5 to about 7.

21. The precursor composition as set forth in claim 19, wherein said stabilizing co-emulsifier is a graft copolymer co-emulsifier is methyl methacrylate copolymer.

22. The precursor composition as set forth in claim 19, wherein said stabilizing co-emulsifier is a comb copolymer co-emulsifier has an HLB value of from about 5 to about 10.

23. The precursor composition as set forth in claim 19, wherein said stabilizing co-emulsifier is a block copolymer co-emulsifier has an HLB value of from about 10 to about 18.

24. The precursor composition as set forth in claim 19, wherein said anionic surfactant is selected from the group consisting of amine, magnesium, potassium, sodium, and zinc salts of alkylbenzene sulfonates, alkylated polyarylphenol phosphate salts, and alkyl naphthalene sulfonates each having an HLB greater than 10.

25. The precursor composition as set forth in claim 19, wherein said co-emulsifier is a hydrophilic lipophilic AB block copolymer.

26. The precursor composition as set forth in claim 1, wherein said co-emulsifier is polyethylene glycol ether.

27. The precursor composition as set forth in claim 1, wherein said solvent is selected from the group consisting of ethers, glycols, and aromatic solvents.

28. The precursor composition as set forth in claim 27, wherein said solvent is propylene glycol monomethyl ether.

29. The precursor composition as set forth in claim 1, wherein said solvent is selected from the group consisting alkyl glycol ethers, aprotic heterocyclic or mono, di-, or polycyclic aromatic solvents having $C_2$-$C_{25}$ carbon atoms, cyclohexanol, hexanol, octanol, butyl glycol, $C_2$-$C_{25}$ mono- and diglycols, polyethylene glycol, glycerol, and $C_3$-$C_{10}$ alkyl carbonates.

30. A stable water based microemulsion pesticide formulation comprising:
a precursor composition comprising—
a quantity of active pesticide ingredients including from about 20% to about 40% by weight of an auxin ester, from about 0.5% to about 3% by weight of a protox inhibitor compatible with the auxin ester, and from about 5% to about 12% by weight of an auxin acid stabilizing agent; and an amount of inactive agents including from about 25% to about 35% by weight of a microemulsifier, from about 8% to about 12% by weight of a stabilizing co-emulsifier for the pesticides, and from about 7% to about 12% by weight of a solvent for the pesticides, said precursor composition being dispersed in an amount of dilution water, the amount of the inactive ingredients being sufficient relative to the quantity of the active pesticide ingredients to cause the precursor composition to spontaneously form a microemulsion having particles that are no larger than 10μ when the precursor composition is diluted with water.

31. The microemulsion as set forth in claim 30, wherein is included from about 3% to about 5% by weight of a dispersant for said pesticides.

32. The microemulsion as set forth in claim 30, wherein said particles are of a size no greater than 2μ.

33. The microemulsion as set forth in claim 30, wherein is provided about 2 parts of water for each about 1.5 parts of said particles dispersed therein.

34. The precursor composition as set forth in claim 1, wherein the volatile organic content is no greater than 2% by weight.

35. The precursor composition as set forth in claim 1, wherein the pH is no greater than 6.

36. The precursor composition as set forth in claim 35, wherein is included a basifying agent.

37. The precursor composition as set forth in claim 36, wherein said basifying agent is selected from the group of mineral bases, organic nitrogen bases of linear and branched $C_1$-$C_9$ alkyl amines, and organic $C_4$-$C_{10}$ heterocyclic $N_1$-$N_3$ amine bases.

38. The precursor composition as set forth in claim 37, wherein said alkyl amines are selected from the group of dimethyl amine, triethylamine, and isopropylamine.

39. The precursor composition as set forth in claim 37, where in said basifying agent amine is 1,2-benzisothiazolin-3-one.

40. The method of inhibiting pests comprising the step of applying to the pests or adjacent the locale of said pests an effective amount of the microemulsion pesticide of claim 31.

* * * * *